United States Patent
Hartlaub

[19]

[11] Patent Number: 6,134,470
[45] Date of Patent: Oct. 17, 2000

[54] METHOD AND APPARATUS FOR TREATING A TACHYARRHYTHMIC PATIENT

[75] Inventor: Jerome T. Hartlaub, New Brighton, Minn.

[73] Assignee: Medtronic, Inc., Minneapolis, Minn.

[21] Appl. No.: 09/188,603

[22] Filed: Nov. 9, 1998

[51] Int. Cl.[7] ............................................. A61N 1/36
[52] U.S. Cl. .................................... 607/14; 607/15
[58] Field of Search .................. 607/14, 15, 62, 607/117

[56] References Cited

U.S. PATENT DOCUMENTS

| | | |
|---|---|---|
| 4,044,774 | 8/1977 | Corbin et al. . |
| 4,146,029 | 3/1979 | Ellinwood, Jr. . |
| 4,428,378 | 1/1984 | Anderson et al. . |
| 4,549,556 | 10/1985 | Tarjan et al. . |
| 4,726,380 | 2/1988 | Vollmann et al. . |
| 4,727,877 | 3/1988 | Kallok . |
| 4,830,006 | 5/1989 | Haluska et al. . |
| 4,880,005 | 11/1989 | Pless et al. . |
| 4,903,701 | 2/1990 | Moore et al. . |
| 4,953,551 | 9/1990 | Mehra et al. . |
| 4,987,897 | 1/1991 | Funke . |
| 5,193,550 | 3/1993 | Duffin . |
| 5,199,428 | 4/1993 | Obel et al. . |
| 5,203,326 | 4/1993 | Collins . |
| 5,220,917 | 6/1993 | Cammilli et al. . |
| 5,255,691 | 10/1993 | Otten . |
| 5,292,338 | 3/1994 | Bardy . |
| 5,314,430 | 5/1994 | Bardy . |
| 5,330,505 | 7/1994 | Cohen . |
| 5,330,507 | 7/1994 | Schwartz . |
| 5,334,221 | 8/1994 | Bardy . |
| 5,356,425 | 10/1994 | Bardy et al. . |
| 5,360,441 | 11/1994 | Otten . |
| 5,400,795 | 3/1995 | Murphy et al. . |
| 5,447,519 | 9/1995 | Peterson . |
| 5,464,434 | 11/1995 | Alt . |
| 5,513,644 | 5/1996 | McClure et al. . |
| 5,522,854 | 6/1996 | Ideker et al. . |
| 5,564,434 | 10/1996 | Halperin et al. . |
| 5,607,418 | 3/1997 | Arzbaecher . |
| 5,662,689 | 9/1997 | Elsberry et al. ............................ 607/5 |
| 5,700,282 | 12/1997 | Zabara . |
| 5,755,736 | 5/1998 | Gillberg et al. . |
| 5,792,187 | 8/1998 | Adams . |
| 5,817,131 | 10/1998 | Elsberry et al. ............................ 607/5 |

*Primary Examiner*—Carl H. Layno
*Attorney, Agent, or Firm*—Reed A. Duthler; Harold R. Patton

[57] ABSTRACT

An implantable anti-arrhythmia system which includes a spinal cord stimulator and an implantable heart rhythm monitor, coupled to control the spinal cord stimulator. The implantable heart monitor is adapted to detect the occurrence of tachyarrhythmias or of precursors thereto and in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation. The device in most embodiments is expected to include a mechanism for delivering an electrical anti-tachyarrhythmia therapy such as pacing, cardioversion or defibrillation in response to detection of a tachyarrhythmia. However, in some embodiments the spinal cord stimulator may be the only electrical stimulator included in the system. In those embodiments including electronic heart stimulators for termination of tachyarrhythmias, the device may also include a single or dual chamber bradycardia pacemaker. In alternative embodiments anti-tachyarrhythmia therapy might additionally be delivered by means of an implantable drug pump.

21 Claims, 4 Drawing Sheets

METHOD AND APPARATUS FOR TREATING A TACHYARRHYTHMIC PATIENT

BACKGROUND OF THE INVENTION

The present invention generally relates to an implantable device for treating tachyarrhythmias and more specifically relates to a device employing spinal cord stimulation to treat patients suffering from a variety of tachyarrhythmias.

Spinal cord stimulation has long been employed to treat patients suffering from chronic pain. For example, spinal cord stimulation for pain control is provided by the ITREL® implantable neurostimulators sold by Medtronic, Inc., Minneapolis Minn. It has also been proposed to combine spinal cord stimulation with cardiac monitoring and/or stimulation devices for a variety of purposes. For example, it has been proposed to combine spinal cord stimulation with implantable atrial defibrillators in order to reduce pain associated with delivery of defibrillation shocks. Such devices are disclosed in U.S. Pat. No. 5,817,131 issued to Elsberry et al. and U.S. Pat. No. 5,792,187 issued to Adams. Spinal cord stimulation in conjunction with an implanted pacemaker or heart monitor to treat angina, activated in response to detection of ischemia is proposed in U.S. Pat. No. 5,199,428 issued to Obel et al.

It has also been proposed to combine parasympathetic nerve stimulators with implantable tachyarrhythmia devices. Typically, such devices attempt to either slow intrinsic heart rhythms or decrease heart irritability to facilitate antitachyarrhythmia treatments such as antitachycardia pacing, cardioversion or defibrillation. Such devices are disclosed in U.S. Pat. No. 5,330,507 issued to Schwartz, U.S. Pat. No. 5,334,221 issued to Bardy, U.S. Pat. No. 5,356,425 issued to Bardy et al., U.S. Pat. No. 5,700,282 issued to Zybara and U.S. Pat. No. 5,203,326 issued to Collins. In these devices, nerve stimulation electrodes are placed generally adjacent either the vagal nerves themselves or the ganglionated plexi or "fat pads" located on the heart, associated with parasympathetic enervation of the heart.

SUMMARY OF THE INVENTION

The present invention is an implantable anti-arrhythmia system which includes a spinal cord stimulator and an implantable heart rhythm monitor, coupled to control the spinal cord stimulator. The implantable heart monitor is adapted to detect the occurrence of tachyarrhythmias or of precursors thereto and in response, trigger the operation of the spinal cord stimulator in order to prevent occurrences of tachyarrhythmias and/or as a stand-alone therapy for termination of tachyarrhythmias and/or to reduce the level of aggressiveness required of an additional therapy such as antitachycardia pacing, cardioversion or defibrillation. The device in most embodiments is expected to include a mechanism for delivering an electrical anti-tachyarrhythmia therapy such as pacing, cardioversion or defibrillation in response to detection of a tachyarrhythmia. However, in some embodiments the spinal cord stimulator may be the only electrical stimulator included in the system. In those embodiments including electronic heart stimulators for termination of tachyarrhythmias, the device may also include a single or dual chamber bradycardia pacemaker. In alternative embodiments anti-tachyarrhythmia therapy might additionally be delivered by means of an implantable drug pump.

The heart monitor portion of the device will typically include one or more electrodes on or adjacent to the heart for monitoring the cardiac electrogram in conjunction with tachyarrhythmia or tachyarrhythmia precursor detection circuitry similar to that presently employed in implantable pacemaker/cardioverter/defibrillators. The heart monitor may also include one or more physiologic sensors, such as an oxygen saturation sensor, a blood pressure sensor, a temperature sensor, a physical activity sensor or other sensors which have been proposed for inclusion in implantable anti-arrhythmia devices, the outputs of such sensors being employed to assist in detection of tachyarrhythmias or tachyarrhythmia precursors and/or to regulate bradycardia pacing rate if the device includes bradycardia pacing capabilities. In some embodiments which include a sensor, the device may additionally activate the spinal column stimulator responsive to the sensor, absent detection of tachyarrhythmia or tachyarrhythmia precursors.

In more elaborate embodiments of the present invention, as disclosed below, the device may take the form of an implantable dual chamber pacemaker/cardioverter/defibrillator which includes a spinal cord stimulator which operates in conjunction with the pacemaker/cardioverter/defibrillator both to prevent occurrences of arrhythmias and to terminate detected arrhythmias. In such devices, or in devices delivering alternative anti-tachyarrhythmia therapies, the spinal cord stimulator may be activated in response to detection of an arrhythmia precursor in an attempt to avoid occurrence of the tachyarrhythmia. The spinal cord stimulator may also be activated after detection of a tachyarrhythmia, in an attempt to terminate the detected tachyarrhythmia. In the absence of termination of the tachyarrhythmia in response to spinal cord stimulation alone, the device may deliver antitachycardia pacing, cardioversion or defibrillation pulses or other anti-tachyarrhythmia therapies. In this case the desired benefit that the preceding period of spinal cord stimulation is reduction of the difficulty of terminating the tachyarrhythmia, allowing a less aggressive therapy to be delivered, such as delivery of antitachycardia pacing where cardioversion might otherwise be required or delivery of cardioversion or defibrillation pulses of lesser amplitude than would otherwise be required.

Preferably the spinal cord stimulator is activated for a predetermined time period in response to detection of a tachyarrhythmia or tachyarrhythmia precursor. At the expiration of this time period, the heart monitor portion of the device checks to determine whether the detected tachyarrhythmia or tachyarrhythmia precursor has terminated. If not, depending on the severity of the detected condition, the device may deliver spinal cord stimulation for a subsequent time period at different pulse parameters or may proceed to deliver an anti-tachyarrhythmia therapy to the heart. In embodiments in which spinal cord stimulation is the only available anti-tachyarrhythmia therapy the device may simply activate the spinal cord stimulator for as long as the tachyarrhythmia persists.

In the event anti-tachycardia therapies in addition to spinal cord stimulation are provided, it is also preferred that either in response to detection of a tachyarrhythmia requiring an immediate response such as ventricular fibrillation or a sufficiently rapid ventricular tachycardia during one of the defined time periods for spinal cord stimulation, that additional therapy will be delivered without waiting for expiration of the defined time period. Correspondingly it is also preferable that if such a device detects a tachyarrhythmia requiring immediate response without prior activation of the spinal cord stimulator, the additional therapy will be delivered without preceding spinal cord stimulation. Spinal cord stimulation in such cases may optionally be delivered concurrent with the additional therapy.

DETAILED DESCRIPTION OF THE PREFERRED EMBODIMENTS OF THE INVENTION

Figure 1:
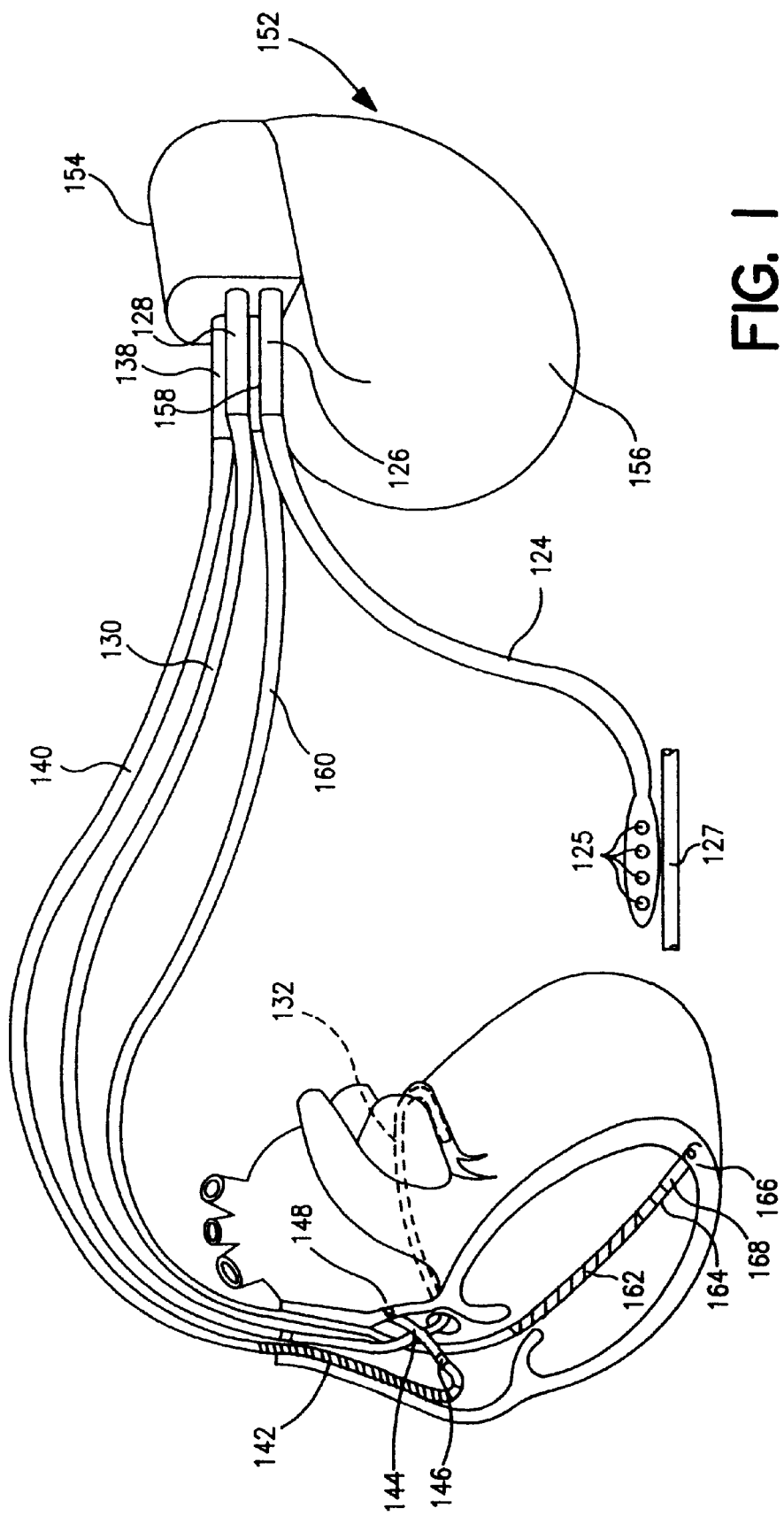
FIG. 1 is a drawing illustrating an automatic atrial and ventricular anti-arrhythmia device incorporating the present invention and its inter-relation to a patient's heart and spinal cord.

FIG. 1 illustrates a fully implantable atrial/ventricular anti-arrhythmia device including a spinal cord stimulation (SCS) system, embodying the present invention, shown in association with a schematically illustrated human heart. The device comprises a pacemaker/cardioverter/defibrillator and spinal cord stimulation system, including a pulse generator 152 (containing the circuit 300 of FIG. 2) and a lead set, including a spinal cord stimulation lead 124, a coronary sinus (CS) lead 130, a right atrial/superior vena cava (RA/SVC) lead 140, and a right ventricular (RV) lead 160.

The ventricular lead 160 may take the form of the ventricular leads disclosed in the U.S. Pat. No. 5,292,338 issued to Bardy or U.S. Pat. No. 5,314,430, also issued to Bardy and incorporated herein by reference in its entirety. The lead body includes three mutually insulated coiled or stranded wire conductors. A ring electrode 164 and an extendible helix tip electrode 166, mounted retractably within an insulating electrode head 168, are located adjacent the distal end of the lead 160 and form a ventricular pace/sense, bipolar electrode pair. An elongated, exposed coil cardioversion electrode 162 is located proximally to electrode head 168 and within the right ventricle. The RV electrode 162 may be fabricated from platinum, platinum alloy or other materials known to be usable in implantable defibrillation electrodes and may be about 5.0 cm in length. Electrodes 164 and 166 are employed for ventricular cardiac pacing and for sensing ventricular depolarizations or R-waves as described above. Each of the electrodes 162, 164, and 166 is coupled to one of the coiled conductors within the ventricular lead 160 which are coupled to three respective electrical connectors in an in-line connector 158 which is in turn attached to receptacles in a connector block 154. Connector 158 and connector block 154 may be constructed according to the teaching of Allowed U.S. Pat. No. 5,843,141 by Ries et al, filed Apr. 25, 1997, for a Medical Lead Connector System, incorporated herein by reference in its entirety.

The RA/SVC lead 140 is constructed in a similar manner and includes a J-shaped distal end with a ring electrode 146 and an extendable helix electrode 148, mounted retractably within an insulating electrode head 144, forming an atrial pace/sense, bipolar electrode pair. Each of the electrodes 146 and 148 are coupled to one of the coiled conductors within the body of the RA/SVC lead 140 and are employed for atrial pacing and for sensing atrial depolarizations. An elongated, exposed coil atrial cardioversion electrode 142 is also provided, proximal to electrode 146 and coupled to the third conductor within the body of RA/SVC lead 144. Electrode 142 preferably may be about 5.0 cm in length or greater and is configured to extend from the SVC into the RA and toward the tricuspid valve. An in-line connector 138 which carries three electrical connectors, each coupled to one of the coiled conductors, is formed at the proximal end of the RA/SVC lead 140 for connection into receptacles of connector block 154.

The CS lead 130 takes the form of the coronary sinus lead disclosed in the above-referenced '430 patent, and includes a single coiled wire conductor, coupled to an elongated, exposed coil defibrillation electrode 132. Electrode 132, illustrated in broken outline, is located within the coronary sinus and great vein of the heart 10 and may also be about 5.0 cm long. A connector 128 is coupled to the coiled conductor of the CS lead 130 and inserted into a further receptacle of the connector block 154.

Optionally, insulation of the outward facing portion of the housing 156 of the pulse generator 152 may be provided using a plastic coating, for example parylene or silicone rubber, as is currently employed in some unipolar cardiac pacemakers. However, the inward facing portion may instead be left uninsulated, or some other division between insulated and uninsulated portions may be employed, to be used as a subcutaneous cardioversion/defibrillation electrode alone or in combination with one or more of the lead bearing cardioversion/defibrillation electrodes to cardiovert or defibrillate either the atria or ventricles. It should be noted that the leads and electrode systems as described to this point in regard to FIG. 1 are comprehensive of atrial and ventricular electrode systems and cardioversion/defibrillation pathways that may be combined or separated depending on whether atrial or ventricular cardioversion/defibrillation therapy is undertaken in conjunction with spinal cord stimulation in accordance with the present invention.

Figure 3:
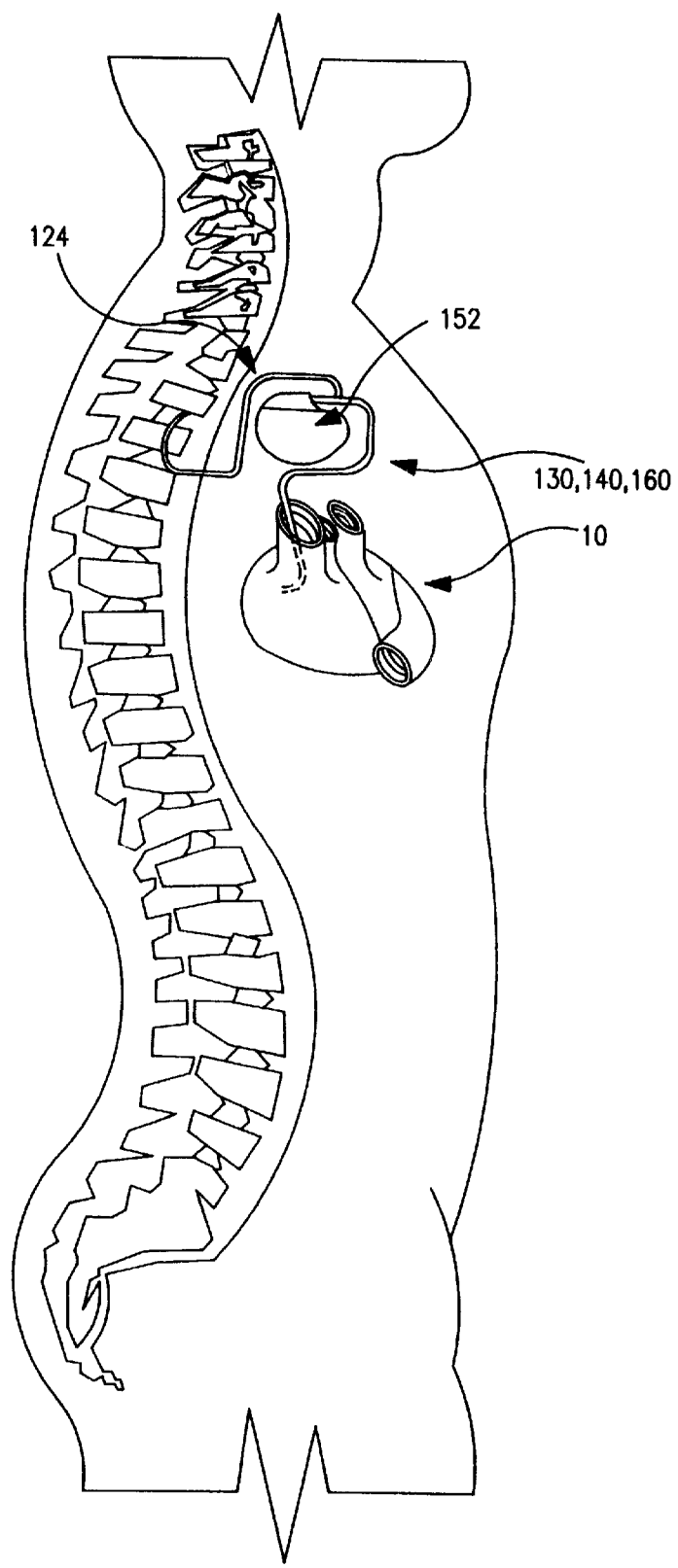
FIG. 3 is an illustration of the system of FIGS. 1 and 2 implanted in a patient.

The SCS lead 124 may be of the type described in U.S. Pat. No. 4,549,556 issued to Tarjan et al. or in commonly assigned U.S. Pat. No. 5,255,691 issued to Otten, U.S. Pat. No. 4,044,774 issued to Corbin et al. or U.S. Pat. No. 5,360,441 issued to Otten, all incorporated herein by reference in their entireties or may correspond to commercially available spinal cord stimulation leads such as the Medtronic® Model 3487A or 3888 leads which include a plurality, e.g. four spaced apart distal electrodes 125 that are adapted to be placed adjacent the spinal cord 127, for example in the intrathecal space or in the epidural space as indicated in FIG. 3 or adjacent the roots of nerves branching off of the spinal cord. The proximal end of the SCS lead 124 carries a quadripolar in-line connector assembly 126, inserted into connector block 154 and coupled to an SCS pulse generator located within housing 156. Two or more of the electrodes may be employed to stimulate the spinal column or a single electrode may be employed in conjunction with an uninsulated portion of the device housing. Leads with fewer or more than four electrodes may of course also be employed.

Figure 2:
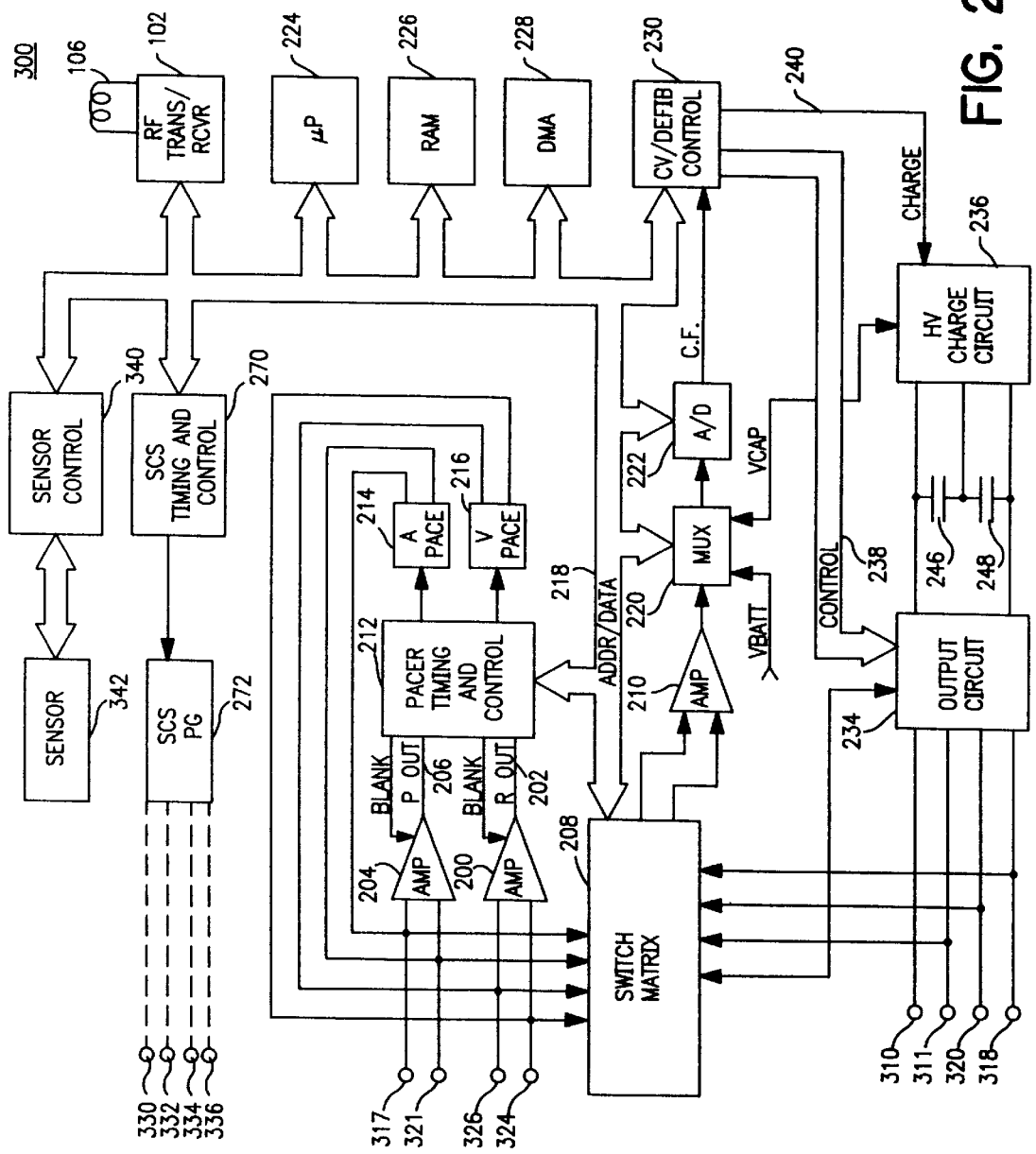
FIG. 2 is a schematic block diagram of an automatic atrial and ventricular anti-arrhythmia device incorporating the present invention.

FIG. 2 is a functional schematic block diagram of an implantable, comprehensive atrial and/or ventricular pacemaker/cardioverter/defibrillator and spinal cord stimulator in which the present invention may usefully and be practiced. This circuit diagram should be taken as exemplary of one type of system in which the invention may be embodied, and not as limiting, as it is believed that the invention may usefully be practiced in a wide variety of device implementations, including atrial and/or ventricular cardioverter/defibrillators which do not provide anti-tachycardia and bradycardia pacing therapies, anti-tachyarrhythmia devices which employ only pacing level therapies or spinal cord stimulators which monitor heart rhythms and employ spinal cord stimulation as the only tachyarrhythmia prevention or termination therapy. In additional alternative embodiments tachyarrhytlmia therapy in the form of drugs delivered by implantablc drug dispensers may be added to or substituted for the electrical anti-tachyarrhythmia therapy provided by the device of FIG. 2. Exemplary implantable drug delivery systems adapted to deliver anti-tachyarrhythmia drugs are disclosed in U.S. Pat. No. 5,607,418, issued to Arzbaecher, U.S. Pat. No. 5,220,917, issued to Cammilli, U.S. Pat. No. 4,146,029, issued to Ellinwood and U.S. Pat. No. 5,330,505, issued to Cohen, all incorporated herein by reference in their entireties.

With this understanding in mind, the circuit 300 of FIG. 2 will be described in conjunction with the lead system of FIG. 1. The circuit 300 is provided with terminals in the receptacles of connector block 154 for making electrical connection with the lead connectors 126, 128, 138 and 158. Terminal 310 is optionally coupled to the uninsulated housing electrode 156. Terminal 320 is attached to RV lead connector 158, and specifically makes connection with the RV electrode 162. Terminal 311 is adapted to make electrical connection with RA/SVC cardioversion electrode 142 through lead connector 138 and RA/SVC lead 140. Terminal 318 is adapted to make electrical connection with CS cardioversion electrode 132 through lead connector 128 and CS lead 130.

Terminals 310, 311, 318 and 320 are coupled to high voltage output circuit 234 which includes high voltage switches controlled by cardioversion/defibrillation control logic 230 via control bus 238. The switches within circuit 234 control which cardioversion electrode sets are employed and which are coupled to the positive and negative terminals of the high voltage output capacitor bank including capacitors 246 and 248 during delivery of the cardioversion shocks.

Terminals 324 and 326 are adapted to make electrical connection through connector 158 of RA lead 160 with the ventricular pace/sense electrode pair 164, 166. Terminals 324 and 326 are coupled to the R-wave sense amplifier 200, which preferably takes the form of an automatic gain controlled amplifier providing an adjustable sensing threshold as a function of the measured R-wave amplitude. A V-SENSE signal is generated on R-out line 202 whenever the signal sensed between electrodes 164 and 166 exceeds the present sensing threshold.

Terminals 317 and 321 are adapted to make electrical connection through connector 138 of RA/SVC lead 140 with the atrial pace/sense electrode pair 146, 148. Terminals 317 and 321 are coupled to the P-wave sense amplifier 204, which preferably also takes the form of an automatic gain controlled amplifier providing an adjustable sensing threshold as a function of the measured P-wave amplitude. An A-SENSE signal is generated on P-out line 206 whenever the signal sensed between terminals 317 and 321 exceeds the present sensing threshold.

Switch matrix 208 is used to select which of the available terminals are coupled to wide band (0.5–200 Hz) amplifier 210 for use in digital signal analysis. Selection of electrodes is controlled by the microprocessor 224 via data/address bus 218, which selections may be varied as programmed-in through RF transmitter receiver 102 and stored in RAM 226. Signals from the electrodes selected for coupling to bandpass amplifier 210 are provided to multiplexer 220, and thereafter are converted to multi-bit digital signals by A/D converter 222, for storage in RAM 226 under control of direct memory access circuit 228. Microprocessor 224 may employ digital signal analysis techniques to characterize the digitized signals stored in random access memory 226 to recognize and classify the patient's heart rhythm employing any of the numerous signal processing methodologies known to the art.

The pacer timing/control circuit 212 includes programmable digital counters which control the basic time intervals associated with DDD, VVI, DVI, VDD, AAI, DDI and other modes of single and dual chamber pacing well known to the art. Circuit 212 also controls escape intervals associated with anti-tachyarrhythmia pacing in both the atrium and the ventricle, employing any anti-tachyarrhythmia pacing therapies known to the art.

Intervals defined by pacing circuit 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 226, in response to stored data in RAM 226 and are communicated to the pacing circuit 212 via address/data bus 218. Pacer circuit 212 also determines the amplitude of the cardiac pacing pulses under control of microprocessor 224.

During pacing, the escape interval counters within pacer timing/control circuit 212 are reset upon sensing of R-waves and P-waves as indicated by signals on lines 202 and 206, and in accordance with the selected mode of pacing on timeout trigger generation of pacing pulses by pacer output circuit 214 and 216, which are coupled to terminals 317, 321, 324 and 326. The escape interval counters are also reset on generation of pacing pulses, and thereby control the basic timing of cardiac pacing functions, including anti-tachyarrhythmia pacing. The durations of the intervals defined by the escape interval timers are determined by microprocessor 224, via data/address bus 218. The value of the count present in the escape interval counters when reset by sensed R-waves and P-waves may be used to measure the durations of R—R intervals, P—P intervals, P–R intervals and R–P intervals, which measurements are stored in memory 226 and used to detect the presence of tachyarrhythmias.

Microprocessor 224 operates as an interrupt driven device under control of programming stored in read only memory (ROM) included therein and is responsive to interrupts from pacer timing/control circuit 212 corresponding to the occurrence sensed P-waves and R-waves and corresponding to the generation of cardiac pacing pulses and nerve stimulation pulses. These interrupts are provided via data/address bus 218. Any necessary mathematical calculations to be performed by microprocessor 224 and any updating of the values or intervals controlled by pacer timing/control circuit 212 take place following such interrupts.

For example, in response to a sensed or paced ventricular depolarization or R-wave, the intervals separating that R-wave from the immediately preceding R-wave, paced or sensed (R—R interval) and the interval separating the paced or sensed R-wave from the preceding atrial depolarization, paced or sensed (P–R interval) may be stored. Similarly, in response to the occurrence of a sensed or paced atrial depolarization (P-wave), the intervals separating the sensed P-wave from the immediately preceding paced of sensed atrial contraction (P—P Interval) and the interval separating the sensed P-wave from the immediately preceding sensed or paced ventricular depolarization (R–P interval) may be stored. Preferably, a portion of the RAM 226 is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R—R or P—P intervals of an average rate indicative of tachyarrhythmia or an unbroken series of short R—R or P—P intervals. The suddenness of onset of the detected high rates, the stability of the high rates, or a number of other factors known to the art may also be measured at this time. Appropriate tachyarrhythmia detection methodologies measuring such factors are described in U.S. Pat. Nos. 4,726,380, 4,880,005, and U.S. Pat. No. 4,830,006, all incorporated herein by reference in their entireties.

A more powerful set of tachyarrhythmia recognition methodologies, which may be employed in a preferred embodiment of the present invention include those described in U.S. Pat. No. 5,755,736 issued to Gillberg et al and incorporated herein by reference in its entirety. As discussed above, in addition to detecting occurrences of tachyarrhythmias, a device according to the present invention may also detect precursors to arrhythmias whereby spinal cord stimulation may be initiated prior to onset of a tachyarrhythmia. In such case, detection of arrhythmia precursors may be accomplished as in U.S. Pat. No. 5,203,326, issued to Collins and also incorporated herein by reference in its entirety.

As computational capacity and speed increases in the context of implantable medical stimulators it is contemplated that devices according to the present invention may also include some capacity for morphological analysis of electrogram waveforms as part of the methodology for detection of tachyarrhythmia and tachyarrhythmia precursors. For example, electrogram morphology analysis systems as proposed in U.S. Pat. No. 5,513,644, issued to McClure et al., U.S. Pat. No. 5,447,519, issued to Peterson, U.S. Pat. No. 5,193,550, issued to Duffin or U.S. Pat. No. 5,400,795, issued to Murphy et al., all incorporated herein by reference in their entireties may usefully be employed in conjunction with the present invention.

Illustrated at 340 and 342 are a physiologic sensor and associated control/processing circuitry, which may optionally be included in a device according to the present invention and employed in conjunction with detection of tachyarrhythmia and tachyarrhythmia precursors. For example, sensor 342 may be an oxygen or pressure sensor mounted on one of the cardiac leads 130, 140 or 160, or a physical activity sensor in conjunction with control and processing circuitry 340 corresponding to that disclosed in U.S. Pat. No. 4,903,701, issued to Moore et al., U.S. Pat. No. 5,564,434, issued to flalperin et al, U.S. Pat. No. 4,428,378, issued to Anderson et al., U.S. Pat. No. 5,464,434, issued to Alt or U.S. Pat. No. 5,330,505, issued to Cohen, all incorporated herein by reference in their entireties may usefully be employed in conjunction with the present invention. However, one of the advantages of the present invention is that it is believed practicable in conjunction with most prior art tachycardia detection algorithms. Sensor 342 may also be employed to derive a measurement of demand for cardiac output and to define a desired bradycardia pacing rate as a function thereof, as is conventional in rate-responsive pacemakers. The sensor defined bradycardia pacing rate may also be compared to the intrinsic heart rate as part of the methodology for detecting tachyarrhythmias or precursors thereto.

In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing and control circuit 212, to control the operation of the escape interval counters therein and to define refractory periods during which detection of R-waves and P-waves is ineffective to restart the escape interval counters.

In the event that generation of a cardioversion or defibrillation shock is required, microprocessor 224 employs an escape interval counter to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuit 230, which initiates charging of the high voltage capacitors 246 and 248 via charging circuit 236, under control of high voltage charging control lines 240 and 242. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuit 212. Following delivery of the fibrillation or tachycardia therapy the microprocessor then returns the device to cardiac pacing and awaits the next successive interrupt due to pacing or the occurrence of a sensed atrial or ventricular depolarization.

In the illustrated device, delivery of the atrial and/or ventricular cardioversion or defibrillation pulses is accomplished by output circuit 234, under control of control circuit 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuits for delivery of biphasic pulse regimens to multiple electrode systems may be found in the above U.S. Pat. Nos. 4,727,877 and 4,953,551 incorporated by reference in their entireties.

In the event that atrial or ventricular fibrillation is identified, the typical therapy will be delivery of a high amplitude defibrillation pulse, typically in excess of 10.0 joules in the case of ventricular fibrillation and about 1.0 joule or less in the case of atrial defibrillation. Lower energy levels will be employed for synchronized cardioversion to convert a high rate tachycardia. As in the case of currently available implantable pacemakers/cardioverter/defibrillators, and as discussed in the above cited references, it is envisioned that the amplitude of the defibrillation pulse may be incremented in response to failure of an initial pulse or pulses to terminate fibrillation.

The atrial cardioverter/SCS delivery system of FIG. 2 includes a spinal cord stimulation pulse generator 272 coupled to terminals 330, 332,334 and 336, which in turn are coupled to two or more of the nerve stimulation electrodes 125 (FIG. 1) via SCS lead 124. In alternative embodiments the device housing may also be employed as an electrode in conjunction with one or more of the electrodes 125. Pulse generator 272 operates under control of microprocessor 224, using timing and control circuitry 270 in a fashion analogous to the operation of timing and control circuitry 212. Operation of the spinal cord stimulation function under control of microprocessor 224 is discussed in more detail in conjunction with FIGS. 4, 5 and six below. The SCS pulse generator may functionally correspond to prior art SCS pulse generators such as those disclosed in any of the references cited in the Background of the Invention above, with control of pulse amplitude, pulse width, burst frequency and inter-burst intervals controlled by microprocessor 224. Pulse parameters may be modified, for example, in response to a failure of delivered spinal cord stimulation to prevent onset of a tachyarrhythmia or failure to terminate a detected tachyarrhythmia.

It should also be noted that in the above-described embodiment, the spinal cord stimulator components 270 and 272 and the lead 124 may be implemented into an implantable medical device separate from the pacemaker/cardioverter/defibrillator circuitry, with the two devices communicating by means of radio signals or otherwise with respect to the delivery of cardioversion therapies and spinal cord stimulation therapies. In such an embodiment, for example, the "Body Bus" system of U.S. Pat. No. 4,987,897 issued to Funke, incorporated herein by reference in its entirety may be employed to communicate commands and status reports between a separately neural stimulation device and a pacemaker/cardioverter/defibrillator or a simpler cardioverter/defibrillator. In such a case, it would be expected that the dual chamber, multi-programmable, pacemaker/cardioverter/defibrillator or the single chamber sub-system thereof would be provide the operating commands to the neural stimulation device.

An external programmer used in conjunction with the device of FIGS. 1 and 2 will include a telemetry transceiver and antenna for a two way telemetry link with the antenna 106 of RF transmitter/receiver 102. Operating modes and parameters may be programmed into or read out of RAM 226 through operation of the telemetry link in a manner well known in the art. In this manner, the pulse amplitudes, frequencies and time intervals for the SCS stimulation therapies described above may be programmed. Data relating to the detection of atrial fibrillation or other arrhythmias or arrhythmia precursors and the delivery of the pacing, cardioversion and defibrillation therapies may also be stored in RAM 226 for telemetry out on command of the external programmer (not shown) in a manner well known in the art.

FIG. 3 is a view of a system according to the present invention as implanted in the body of the patient. The pulse generator 152 is implanted pectorally, with the spinal cord lead 124 implanted such that its electrodes are located adjacent the spinal column, for example in the epidural or intrathecal space, preferably between C6 and T3, more preferably in the vicinity of T1. The cardiac lead system including leads 130, 140 and 160 is implanted in the heart, as illustrated in FIG. 1.

Figure 4:
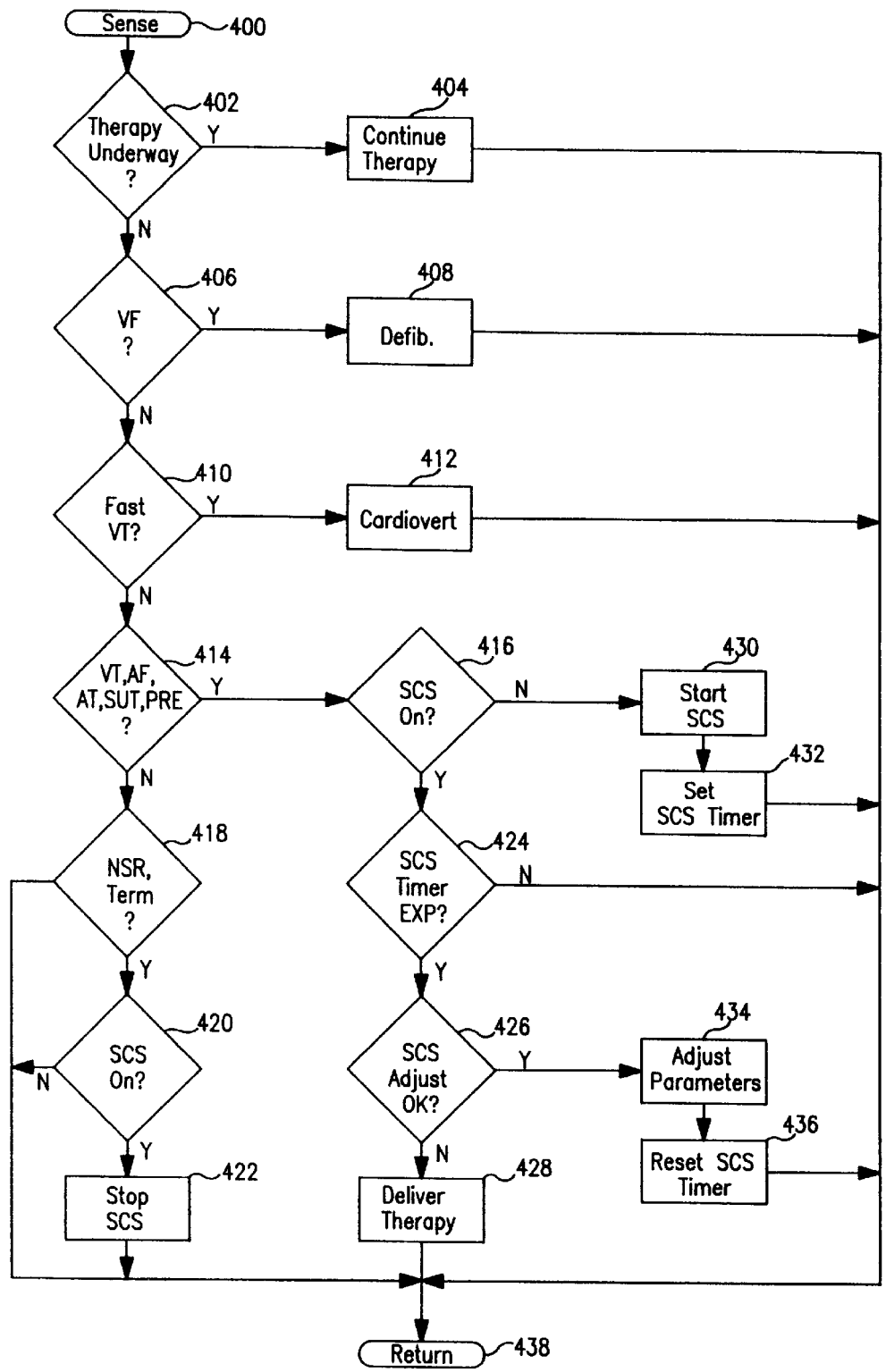
FIG. 4 is a flow chart of the operation of the system of FIGS. 1–3 in response to detection of tachyarrhythmia or tachyarrhythmia precursors.

FIG. 4 is a flow chart illustrating operation of a device as described above which employs the spinal cord stimulator for prevention of tachyarrhythmias, for termination of tachyarrhythmias and to assist in termination of tachyarrhythmias in conjunction with electrical tachyarrhythmia termination therapies applied to the heart. While the described embodiment employs the spinal cord stimulator to perform all three of these functions, it should be understood that the invention may also be practiced using the spinal cord stimulator to perform any of these functions individually or any two of these functions in combination.

It should be understood that the device of FIGS. 1–3 above monitors the rhythm of the patient's heart and may optionally as well provide bradycardia support pacing. Analysis of heart rhythm, as discussed below in conjunction with FIG. 4, takes place in response to sensing of atrial and/or ventricular depolarizations of the heart, and the flow chart of FIG. 4 illustrates the device response to a sensed heart depolarization.

After sensing of an atrial or ventricular depolarization at 400, the device first determines whether it is in the process of delivering an electrical anti-arrhythmia therapy to the heart at 402, if so, the device continues to deliver the therapy at 404 according to its programmed parameters. The therapy under way could be anti-tachyarrhythmia pacing, cardioversion or defibrillation. Assuming that electrical anti-arrhythmia therapy is not presently being delivered to the heart, the device checks at 406 to determine whether the heart's rhythm alone or in conjunction with the output of a physiologic sensor indicates the presence of ventricular fibrillation at 406. If so, the device initiates charging of the high voltage capacitors and delivery of a ventricular fibrillation pulse at 408. Due to the necessity of rapid delivery of therapy in response to detected ventricular fibrillation, the device does not activate delivery of spinal cord stimulation as a condition precedent to delivery of defibrillation therapy at 408. Optionally the device may activate the spinal cord stimulator concurrent with beginning the defibrillation therapy, e.g. concurrent with charging of the high voltage output capacitors in order to effect a reduction in defibrillation threshold.

Similarly, if ventricular fibrillation is not under way, the device checks at 410 to determine whether a ventricular tachycardia of sufficiently rapid rate is under way to require immediate delivery of cardioversion therapy. If so, the device begins charging of the high voltage output capacitors and delivery of cardioversion therapy at 412. Due to the fact that a rapid ventricular tachyarrhythmia may be hemodynamically unstable, the device does not initiate spinal cord stimulation as a condition precedent to delivery of the cardioversion therapy at 412. Optionally the device may activate the spinal cord stimulator concurrent with beginning the electrical therapy, e.g. concurrent with charging of the high voltage output capacitors in order to effect a reduction in cardioversion threshold.

Assuming that a ventricular tachyarrhythmia which requires immediate delivery of electrical therapy to the heart is not under way, the device checks at 414 to determine whether one of a number of other possible conditions warranting activation of the spinal cord stimulator are present. Such conditions could include slower reentrant ventricular tachycardia, atrial fibrillation, reentrant atrial tachycardia, supraventricular tachycardia including reentrant A–V nodal tachycardia, or the presence of tachycardia precursors. The detection of these various tachyarrhythmias may correspond to any of the detection methodologies described in the patents incorporated by reference above. Detection of tachyarrhythmia precursors may take a variety of forms, but preferably includes detection criteria based upon rate and/or order of detected cardiac depolarizations such as including defined frequencies of occurrence of PVC's or couplets. The detection of precursors may alternatively or additionally include a defined degree of progress toward meeting detection criteria for the various tachyarrhythmias. For example, in the context of a device employing a rule based tachycardia detection methodology as in the Gillberg et al patent, incorporated by reference above, which requires simultaneous satisfaction of a plurality of rules to detect occurrence of a tachyarrhythmia, satisfaction of a predefined percentage of the rules or satisfaction of a predefined subset of the rules may serve to serve as an indicator that tachyarrhythmia precursors are present. Alternatively, if the device employs a physiologic sensor as in the Cohen and Alt patents incorporated by reference above, the device may compare the sensor indicated rate with the actual heart rate, and if the actual heart rate exceeds the sensor indicated rate by too great an amount, the device may determine that tachyarrhythmia precursors are present. In the case of a device which operates on the basis of detection of tachycardia by means of a series of high rate beats, as is typically employed in present implantable pacemaker/cardioverter/defibrillators, the device may determine that tachyarrhythmia precursors are present responsive to a sequence of a lesser number of beats of the required high rate or at a rate somewhat below the rate necessary to detect a tachyarrhythmia.

As an optional additional feature, if a sensor is present, for example an intracardiac pressure or oxygen saturation sensor, the device may optionally also check at 414 to determine if the sensor indicates a condition based on factors other than the rate, order or timing of detected depolarizations which would merit activation of the spinal cord stimulator in the absence of a detected tachyarrhythmia. For example, as noted above, in response to a detected amount of increase in intracardiac blood pressure or drop in oxygen saturation, the device may activate the spinal cord stimulator in a manner analogous to that disclosed in the Obel et al. patent cited above.

In the event that either one of the defined tachyarrhythmias or tachyarrhythmia precursors or other sensed condition warranting activation of spinal cord stimulation is determined to be present, at 414, the device then checks at 416 to determine whether spinal cord stimulation is already under way. If not, spinal cord stimulation is initiated at 430 and a spinal cord stimulation timer is set at 432 defining a first predetermined interval, hereafter an "SCS interval" for spinal cord stimulation. The device then awaits occurrence of the next sensed cardiac depolarization, or, if bradycardia pacing is activated, delivery of the next bradycardia pacing pulse at 438.

In the event that spinal cord stimulation is under way at 416, the device determines whether the SCS interval previously in effect has expired at 424. If not, the device simply awaits occurrence of the next sensed cardiac depolarization or delivery of the next cardiac pacing pulse at 438. In the event that the SCS interval has expired at 424, the device checks to determine whether an adjustment to the parameters of the spinal cord stimulator is available at 426. As discussed above, in some cases it may be desirable to attempt to terminate or prevent occurrence of tachyarrhythmias using a predetermined or preprogrammed sequence of spinal cord stimulation pulse parameters applicable over a series of SCS intervals, for example, by increasing amplitude, pulse rate or frequency of the stimulus pulses in the next SCS interval or by selecting a new electrode configuration in response to expiration of the preceding SCS time interval without termination of either a detected tachyarrhythmia or cessation of tachyarrhythmia precursors.

The number of SCS intervals and the types of spinal cord stimulation available preferably varies as a function of the detected arrhythmia, arrhythmia precursor or other define condition for activation of the spinal cord stimulator. For example, in response to atrial or ventricular tachycardia, the device may employ spinal cord stimulation at a preset value, for one SCS time interval, and thereafter, in the absence of termination of a detected arrhythmia, deliver an electrical anti-tachycardia therapy such as antitachycardia pacing or cardioversion. However, in response to a detection of atrial fibrillation, the device might provide spinal cord stimulation over a sequence of two or more SCS intervals, incrementing pulse amplitude, pulse width or pulse frequency and/or changing stimulation electrode configuration with each successive SCS interval up to a maximum number of available intervals. As the urgency of termination of atrial fibrillation or tachyarrhythmia precursors is substantially lower, and the physician may wish to give spinal cord stimulation a greater opportunity to affect termination on its own. On expiration of the last available SCS interval without termination, the device may the deliver an atrial defibrillation pulse. In response to detection of arrhythmia precursors or other defined preconditions in the absence of detection of tachyarrhytlumias the device might either provide SCS stimulation over an unlimited number of SCS intervals or up to a greater number of SCS intervals than available in response to a detected tachyarrhythmia. It is anticipated that the physician will set the available therapy options for each detected tachyarrhythmia or other condition.

If the SCS interval in effect has expired at 424 and according to the programming of the device, a SCS interval is available with modified parameters, the parameters are adjusted at 434 and the SCS timer is reset at 436. The device then returns to await occurrence of the next sensed event or delivery of the next bradycardia pacing pulse. If an SCS interval with adjusted parameters is not available at 426, the device proceeds to deliver an electrical antitachyarrhythmia therapy such as antitachycardia pacing or cardioversion to the patient's heart, if programmed to do so for the detected tachyarrhythmia or tachyarrhythmia precursor, and awaits occurrence of the next sensed depolarization or delivered pacing pulse at 438.

In the event that none of the identified tachyarrhythmias, tachyarrhythmia precursors or other defined conditions are detected at 414, the device checks at 418 to determine whether a return to normal sinus rhythm, indicating a termination of tachyarrhythmias and tachyarrhythmia precursors has occurred. This may be detected, for example, by detection of a number of successive beats below a determined rate, or by detection of a number of successive beats, for example, having a rate which correlates closely to a physiologic sensor, if included in the device. In response to detection of a return to normal sinus rhythm, the device checks at 420 to determine whether spinal cord stimulation is currently activated, and if so, turns the spinal cord stimulator off at 422. The device then returns to await the next sensed event or delivered pacing pulse at 438.

It should be noted that if following initial detection of a tachyarrhythmia or tachyarrhythmia precursor a different tachyarrhythmia is detected, the programming associated with the newly detected condition will take effect. For example, on detection of ventricular fibrillation at 402, regardless whether spinal cord stimulation is underway, a ventricular defibrillation pulse will be delivered. Correspondingly, if a tachyarrhythmia is newly detected which has fewer available SCS intervals, electrical anti-tachyarrhythmia therapy will be delivered on expiration of the number of SCS intervals specified for that newly detected tachyarrhythmia. If such a tachyarrhythmia is detected after the programmed number of SCS intervals for that tachyarrhythmia have already expired, the programmed electrical therapy will be delivered immediately to the patient's heart. In this manner, the device may respond appropriately to arrhythmias of increasing severity.

In conjunction with the present invention, although not illustrated in FIG. 4, it should also be understood that the device may also adjust the parameters of the spinal cord stimulus pulses in response to failure to terminate a detected arrhythmia, arrhythmia precursors or other defined condition following expiration of the available number of SCS intervals, such that upon the next subsequent detection of the same condition, spinal cord stimulation is initiated at a higher pulse amplitude, greater pulse width, higher pulse frequency or with a different electrode configuration.

It should also be understood that, although not illustrated in FIG. 4, in conjunction with the device as described in FIGS. 1–3, it is also possible to program spinal cord stimulation to be activated by the microprocessor continuously or on a time schedule stored in the random access memory independent of detection of tachyarrhythmias or tachyarrhythmia precursors, in a manner analogous to operation of spinal cord stimulators employed for control of chronic pain. For example, the microprocessor 224 may simply employ a real time clock to activate the spinal cord stimulator at a relatively low stimulus pulse amplitude and/or pulse widths on expirations of predetermined intervals, with a view toward generally preventing occurrences of tachyarrhythmias and tachyarrhythmias precursors. In such embodiments operation according to the flow chart of FIG. 4, initiation of spinal cord stimulation in response to one of the defined conditions would be replaced with activation of spinal cord stimulation at different times or at different pulse amplitudes, pulse widths, pulse frequencies or with different electrode configurations.

Variations and modifications to the present invention may be possible given the above disclosure. Although the present invention is described in conjunction with a microprocessor-based architecture, it will be understood that it could be implemented in other technology such as digital logic-based, custom integrated circuit (IC) architecture, if desired. While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

In conjunction with the above disclosure, I claim:

1. An anti-tachyarrhythmia device, comprising:
   a heart monitor comprising a tachyarrhythmia detector;
   a spinal cord stimulator responsively coupled to the heart monitor and activated in response to detection of a reentrant tachycardia by the tachyarrhythmia detector;
   means for delivering an anti-tachyarrhythmia therapy other than spinal cord stimulation in response to failure of spinal cord stimulation to terminate the detected reentrant tachycardia;
   a spinal cord stimulation timer initiated in response to activation of the spinal cord stimulator and defining a spinal cord stimulation interval thereafter and wherein said therapy delivering means is activated responsive to expiration of a spinal cord stimulation interval in conjunction with failure of spinal cord stimulation to terminate the detected reentrant tachycardia.

2. A device according to claim 1 wherein the means for delivering an anti-tachyarrhythmia therapy comprises means for delivering an electrical therapy to a patient's heart.

3. A device according to claim 1 or claim 2 further comprising means for modifying stimulation parameters of the spinal cord stimulator responsive to expiration of a spinal cord stimulation interval in conjunction with failure of spinal cord stimulation to terminate the detected reentrant tachycardia.

4. A device according to claim 1 wherein the heart monitor further comprises a tachyarrhythmia precursor detector and wherein the spinal cord stimulator is further activated in response to detection of tachyarrhythmia precursors by the tachyarrhythmia precursor detector.

5. A device according to claim 4 comprising a spinal cord stimulation timer initiated in response to activation of the spinal cord stimulator and defining a spinal cord stimulation interval thereafter and further comprising means for modifying stimulation parameters of the spinal cord stimulator responsive to expiration of a spinal cord stimulation interval in conjunction with failure of spinal cord stimulation to terminate the detected tachyarrhythmia precursors.

6. A device according to claim 1 or claim 4 wherein the heart monitor comprises a physiologic sensor.

7. A device according to claim 6 wherein the heart monitor comprises means for detecting tachyarrhythmias responsive to the physiologic sensor.

8. A device according to claim 6 wherein the heart monitor comprises means for detecting tachyarrhythmia precursors responsive to the physiologic sensor.

9. A device according to claim 6 wherein the spinal cord stimulator is responsively coupled to the physiologic sensor and is activated in response to the sensor in the absence of detection of tachyarrhythmia by the tachyarrhythmia detector.

10. An anti-tachyarrhythmia device, comprising:
    a heart monitor comprising a tachyarrhythmia precursor detector;
    a spinal cord stimulator coupled to the heart monitor and activated in response to detection of tachyarrhythmia precursors by the tachyarrhythmia precursor detector;
    a spinal cord stimulation timer initiated in response to activation of the spinal cord stimulator and defining a series of successive spinal cord stimulation intervals thereafter and further comprising means for modifying stimulation parameters of the spinal cord stimulator for a spinal cord stimulation interval responsive to expiration of a preceding spinal cord stimulation interval in conjunction with failure of spinal cord stimulation to terminate the detected tachyarrhythmia precursors.

11. A device according to claim 10 wherein the heart monitor comprises a physiologic sensor.

12. A device according to claim 11 wherein the heart monitor comprises means for detecting tachyarrhythmia precursors responsive to the physiologic sensor.

13. A device according to claim 12 wherein the spinal cord stimulator is responsively coupled to the physiologic sensor is activated in response to the sensor in the absence of detection of tachyarrhythmia precursors by the tachyarrhythmia detector.

14. An anti-tachyarrhythmia device, comprising:
    a heart monitor comprising a tachyarrhythmia detector;
    a spinal cord stimulator operable to deliver spinal cord stimulation therapy; and
    means for modifying stimulation parameters of the spinal cord stimulation therapy responsive to detection of a tachyarrhythmia by the tachyarrhythmia detector.

15. A device according to claim 14 further comprising means for delivering an anti-tachyarrhythmia therapy other than spinal cord stimulation in response to failure of spinal cord stimulation to terminate the detected tachyarrhythmia.

16. An anti-tachyarrhythmia device, comprising:
- a heart monitor comprising a tachyarrhythmia precursor detector;
- a spinal cord stimulator operable to deliver spinal cord stimulation therapy; and
- means for modifying stimulation parameters of the spinal cord stimulation therapy responsive to detection of tachyarrhythmia precursors by the tachyarrhythmia precursor detector.

17. A device according to claim 16 further comprising means for further modifying stimulation parameters of the spinal cord stimulation therapy responsive to failure of spinal cord stimulation to terminate the detected tachyarrhythmia precursors.

18. An anti-tachyarrhythmia device, comprising:
- a heart monitor comprising means for detecting a plurality of tachyarrhythmias;
- means for delivering an anti-tachyarrhythmia therapy other than spinal cord stimulation;
- a spinal cord stimulator responsively coupled to the heart monitor and activated in response to detection of a first one of the tachyarrhythmias;
- a spinal cord stimulation timer initiated in response to activation of the spinal cord stimulator and defining a spinal cord stimulation interval thereafter;
- means for activating the anti-tachyarrhythmia therapy delivering means responsive to expiration of a spinal cord stimulation interval in conjunction with failure of spinal cord stimulation to terminate the detected tachyarrhythmia; and
- means responsive to detection of a second one of the tachyarrhythmias for activating the anti-tachyarrhythmia therapy delivering means independent of expiration of any spinal cord stimulation interval.

19. A device according to claim 18 wherein the means for delivering an anti-tachyarrhythmia therapy comprises means for delivering an electrical therapy to a patient's heart.

20. A device according to claim 18 or claim 19 comprising means for activating the spinal cord stimulator responsive to detection of the second one of the tachyarrhythmias, concurrent with activation of the anti-tachyarrhythmia therapy delivering means.

21. A device according to claim 20 wherein the anti-tachyarrhythmia therapy delivering means comprises means for delivering first and second anti-tachyarrhythmia therapies and wherein the means for activating the anti-tachyarrhythmia therapy delivering means responsive to expiration of a spinal cord stimulation interval comprises means for activating the anti-tachyarrhythmia therapy delivering means to deliver the first anti-tachyarrhythmia therapy and wherein the means for activating the anti-tachyarrhythmia therapy delivering means independent of expiration of any spinal cord stimulation interval comprises means for activating the anti-tachyarrhythmia therapy delivering means to deliver the second anti-tachyarrhythmia therapy.

* * * * *